US011526981B2

United States Patent
Oh et al.

(10) Patent No.: US 11,526,981 B2
(45) Date of Patent: Dec. 13, 2022

(54) ECOTOXICITY EVALUATION ANALYZING DEVICE INCLUDING MICROALGAE IMAGE ANALYSIS PROGRAM INSTALLED THEREIN, AND METHOD THEREOF

(71) Applicants: KOREA INSTITUTE OF OCEAN SCIENCE & TECHNOLOGY, Busan (KR); KOREA UNIVERSITY RESEARCH AND BUSINESS FOUNDATION, SE-JONG CAMPUS, Sejong-si (KR)

(72) Inventors: Sang-Woo Oh, Sejong-si (KR); Moon-Jin Lee, Daejeon (KR); Sungkyu Seo, Sejong-si (KR); Dongmin Seo, Seoul (KR); Sanghoon Shin, Seoul (KR)

(73) Assignees: KOREA INSTITUTE OF OCEAN SCIENCE & TECHNOLOGY, Busan (KR); KOREA UNIVERSITY RESEARCH AND BUSINESS FOUNDATION, SE-JONG CAMPUS, Sejong-Si (KR)

( * ) Notice: Subject to any disclaimer, the term of this patent is extended or adjusted under 35 U.S.C. 154(b) by 301 days.

(21) Appl. No.: 16/761,753

(22) PCT Filed: Nov. 6, 2018

(86) PCT No.: PCT/KR2018/013391
§ 371 (c)(1),
(2) Date: May 5, 2020

(87) PCT Pub. No.: WO2019/093741
PCT Pub. Date: May 16, 2019

(65) Prior Publication Data
US 2020/0279370 A1    Sep. 3, 2020

(30) Foreign Application Priority Data
Nov. 8, 2017 (KR) .................. 10-2017-0148107

(51) Int. Cl.
    G06T 7/00    (2017.01)
    C12Q 1/02    (2006.01)
(52) U.S. Cl.
    CPC ............ *G06T 7/0012* (2013.01); *C12Q 1/02* (2013.01); *G06T 2207/10056* (2013.01)
(58) Field of Classification Search
    None
    See application file for complete search history.

(56) References Cited

U.S. PATENT DOCUMENTS

2016/0041094 A1    2/2016    Lei

FOREIGN PATENT DOCUMENTS

| KR | 10-2002-0006812 A |   | 1/2002 |           |
|----|-------------------|---|--------|-----------|
| KR | 20020006812 A     | * | 1/2002 | G01B 11/303 |

(Continued)

OTHER PUBLICATIONS

Geonsoo Jin, In-Hwa Yoo, Seung Pil Pack, Ji-Woon Yang, Un-Hwan Ha, Se-Hwan Paek, Sungkyu Seo, Lens-free shadow image based high-throughput continuous cell monitoring technique, Biosensors and Bioelectronics, vol. 38, Issue 1, 2012, pp. 126-131, ISSN 0956-5663 (Year: 2012).*
Machine translation of KR20120087563A1 (Year: 2012).*
Machine translation of KR101463006B1 (Year: 2014).*

(Continued)

*Primary Examiner* — Vu Le
*Assistant Examiner* — Courtney Joan Nelson
(74) *Attorney, Agent, or Firm* — Lewis Roca Rothgerber Christie LLP (57) ABSTRACT

The present invention relates to an ecotoxicity evaluation analysis device installed with a microalgae image analysis (Continued)

program therein for analyzing the microalgae 1 and evaluating and analyzing ecotoxicity, the device comprising: a complementary metal oxide semiconductor unit 10 having an arranging part 15 on the top for positioning the microalgae 1 and installed with a microalgae image analysis program therein for photographing a microscopic image and a shadow image of the microalgae 1 and analyzing the images; and a light emitting diode unit 20 for irradiating a light source to the microalgae 1 located in the arranging part 15 of the complementary metal oxide semiconductor unit 10.

11 Claims, 7 Drawing Sheets

(56) References Cited

FOREIGN PATENT DOCUMENTS

| KR | 10-1102310 B | 1/2012 | | |
|---|---|---|---|---|
| KR | 10-2012-0087563 A | 8/2012 | | |
| KR | 20120087563 A1 * | 8/2012 | ........... | G01N 33/483 |
| KR | 10-1197101 B | 11/2012 | | |
| KR | 10-1303617 B | 9/2013 | | |
| KR | 10-1463006 B | 11/2014 | | |
| KR | 101463006 B1 * | 11/2014 | ........... | G06T 7/0002 |
| KR | 10-1484732 B | 1/2015 | | |
| KR | 10-2015-0089402 A | 8/2015 | | |

OTHER PUBLICATIONS

Machine translation of KR20020006812A (Year: 2002).*
Machine translation KR 20190009504 (Year: 2018).*

* cited by examiner

ECOTOXICITY EVALUATION ANALYZING DEVICE INCLUDING MICROALGAE IMAGE ANALYSIS PROGRAM INSTALLED THEREIN, AND METHOD THEREOF

CROSS-REFERENCE TO RELATED APPLICATION(S)

This application is a National Phase Patent Application of International Patent Application Number PCT/KR2018/013391, filed on Nov. 6, 2018, which claims priority of Korean Patent Application No. 10-2017-0148107, filed Nov. 8, 2017, the entire contents of both of which are incorporated herein by reference.

TECHNICAL FIELD

The present invention relates to an ecotoxicity evaluation analysis device and method thereof, and the present invention relates to a device and method for evaluating and analyzing ecotoxicity, more particularly, to an ecotoxicity evaluation analysis device installed with a microalgae image analysis program therein, comprising a complementary metal oxide semiconductor including a technique for recognizing a change in the state of microalgae that occurs when exposed to a toxic substance, and a light emitting diode, and a method thereof.

BACKGROUND ART

Conventionally, for environmental analysis, toxic substances were quantitatively analyzed by applying a physicochemical analysis technique. However, for the physicochemical analysis technique, it is practically impossible to analyze a wide measurement area in terms of cost, time, technology and manpower. Therefore, ecotoxicity evaluation and analysis technology has emerged as a scientific and efficient management method for environmental analysis.

The ecotoxicity evaluation and analysis technology is a technology that evaluates the potential hazards of substances present in the environment by using organisms. This technology can capture information about damage caused when a foreign substance used is concentrated in an organism, or bioavailability that may occur when various compounds coexist.

Internationally, an ecotoxicity evaluation technology using a variety of test species such as daphnia, fish and algae has been approved by institutions such as ISO, OECD, ASTM, NIWA and US EPA, and it has been certified as a new technology. In South Korea, an ecotoxicity evaluation are being conducted using the evaluation technology recommended by the above institutions, and research on domestic species that has passed international certification is actively conducted.

In the research on analysis technology, the technology itself is evolving in a practical direction, such as supplementing the disadvantages of the conventional physicochemical analysis technology, reducing the size of the utilization space, making use of expensive equipment unnecessary, and simplifying the applied procedure. Nevertheless, in order to derive the analytical results, it is a practice to rely on a manual analysis device for microscopically analyzing the type, counting, and state of test biological species.

Therefore, the development of analysis technology that has evolved in terms of time, techniques, and manpower required for analysis, and the research into an evolved ecotoxicity analysis device separated from a microscope-based manual analysis device are needed.

Currently, various studies are being conducted to develop ecotoxicity evaluation as an international standard test method, but the device for analyzing the ecotoxicity evaluation is still limited to a microscope-based manual analysis.

In addition, the manual analysis device takes a lot of time for measurement and requires an expert capable of evaluating ecotoxicity, and even though analyzed by an expert, an error of the analysis coefficient is quite large.

DETAILED DESCRIPTION OF THE INVENTION

Technical Problem

The present invention has been designed to solve the above-mentioned problems, and, therefore, an object thereof is to provide an ecotoxicity evaluation analysis device installed with an automated microalgae image analysis program therein using a complementary metal oxide semiconductor and a light emitting diode, and a method thereof.

Another object of the present invention is to solve the above-mentioned problems, and in particular, to provide an ecotoxicity evaluation analysis device installed with an automated microalgae image analysis program therein, which includes a technology capable of analyzing a state of the microalgae and thus, provides users with various research and analysis results, and a method thereof.

Technical Solution

The microalgae image analysis program may utilize an automated image analysis technique.

Preferably, the microalgae image analysis program can classify and analyze the microalgae into a healthy state, a cyst state, and a dead state, respectively.

The present invention for achieving the above object may relate to a computer-readable recording medium which stores a program for implementing an analysis method using an ecotoxicity evaluation analysis device installed with a microalgae image analysis program therein.

The details of other embodiments are included in the following "Detailed Description of the Embodiments" and the attached "Drawings".

Advantages and/or features of the present invention and methods for achieving them will become apparent with reference to various embodiments described below in detail in conjunction with the accompanying drawings.

However, it is to be noted that the present invention is not limited to the configuration of each embodiment disclosed below, but may also be implemented in various different embodiments; that the respective embodiments disclosed herein is provided only to make the disclosure of the present invention complete, and only to enable those skilled in the art to fully understand the scope of the present invention; and that the scope of the present invention is defined only by each of the claims.

Advantageous Effects

According to the present invention, a microalgae measurement device using a complementary metal oxide semiconductor and a light emitting diode does not require an expensive light source, optical stage and optical lens, and thus, the device can be manufactured at low cost.

According to the present invention, since an image taken with a complementary metal oxide semiconductor unit is analyzed by image processing technology, it is possible to develop an automated analysis system. This drastically reduces the time spent for measurement by experts capable of evaluating ecotoxicity.

According to the present invention, by means of a complementary metal oxide semiconductor, the image is photographed in real time and the photographed image is analyzed, thereby eliminating the need for a process and reagent for fixing microalgae (removing flagellar function).

According to the present invention, a technology capable of analyzing the state of microalgae can classify and analyze the microalgae into a healthy state, a cyst state, and a dead state, respectively.

The technology of the present invention facilitates the classification of the microalgae between healthy and cyst states occurring in the manual counting process which is currently performed by expert, and can classify the microalgae in a dead state through a dyeing process, without a dyeing process.

According to the present invention, it is possible to automate cell state analysis and develop a dye-free device through the microalgae state analysis technology.

According to the present invention, the microalgae state analysis technology dramatically shortens the time for analyzing the effects of toxic substances on the microalgae as well as the measurement time in a 96-hour acute analysis performed during the conventional ecotoxicity evaluation.

The current ecotoxicity evaluation measures the number of dead individuals or the number of living individuals and analyzes them to derive results. According to the present invention, however, since the present technology can analyze changes in the state of microalgae that occur when exposed to toxic substances, it can provide various research data that were not available in the past. For example, the present invention can be applied to a study on the mechanism by which the microalgae do not die and recover depending on the concentration of toxic substances, a study on the recovery ability of microalgae, etc.

DETAILED DESCRIPTION OF THE EMBODIMENTS

Hereinafter, preferred embodiments of the present invention will be described in detail with reference to the accompanying drawings.

Before describing the present invention in detail, it is to be noted that the terms or words used herein should not be interpreted as being unconditionally limited to a conventional or dictionary meanings; that the present inventors can properly define and use various terminology concepts in order to explain the invention in the best way; and that furthermore, these terms or words should be interpreted as meanings and concepts consistent with the technical spirit of the present invention.

That is, it is to be noted that the terms used herein are only used to describe preferred embodiments of the present invention, and are not intended to specifically limit the content of the present invention; and that these terms are defined in consideration of various possibilities of the present invention.

In addition, it should be noted that a singular expression as used herein may include a plural expression, unless the context clearly indicates otherwise; and that similarly, even if expressed in plural, it may include the meaning of the singular.

When describing the invention as "including" certain component throughout the specification, it may mean that any other components may be further included but not excluded, unless otherwise specified.

Furthermore, it is to be noted that when a component is described as being "existing in or connected to" other component(s), the component may be directly connected to the other component(s), or may be installed in contact with or at a distance from the other component(s); and in case the component is installed apart from the other component(s), there may be a third component or means for fixing or connecting the component to other component(s), but a description thereof may be omitted.

On the other hand, if a component is described as being "directly connected" or "directly coupled" to another component, it should be understood that there are no third components or means.

Similarly, it should be understood that other expressions describing the relationship between each component, such as "between~" and "immediately between~", or "neighboring to~" and "directly neighboring to~" have the same meanings as above.

In addition, it is to be noted that as used herein, the terms such as "one surface", "other surface", "one side", "other side", "first", "second", etc. are used to clearly distinguish one component from another component, and the meaning of the concerned component is not limited by such terms.

In addition, if used in this specification, the terms related to positions such as "upper", "lower", "left", "right" and the like should be understood as indicating the relative position of the relevant elements in the drawings, not as referring to an absolute position, unless otherwise specified.

Moreover, it should be noted that as used herein, the terms such as "unit", "part", "module", and "device" refer to a unit capable of processing one or more functions or operations, which may be implemented in hardware or software, or in a combination thereof.

In addition, in connection with reference numerals indicating each component in the drawings, the same reference numerals are used for the same components even though they are indicated in different drawings. That is, the same reference numerals used throughout the specification indicate the same components.

In the accompanying drawings, the size, position, and coupling relationship of each component constituting the present invention may be partially exaggerated, reduced, or omitted in order to make the spirit of the present invention clearly understood or for convenience of explanation, and, therefore, the proportion or scale may not be strict.

In addition, in the following description of the present invention, a detailed description of a configuration considered to make the subject matter of the present invention unnecessarily obscure, for example, a known art including a conventional technology may be omitted.

Figure 1:
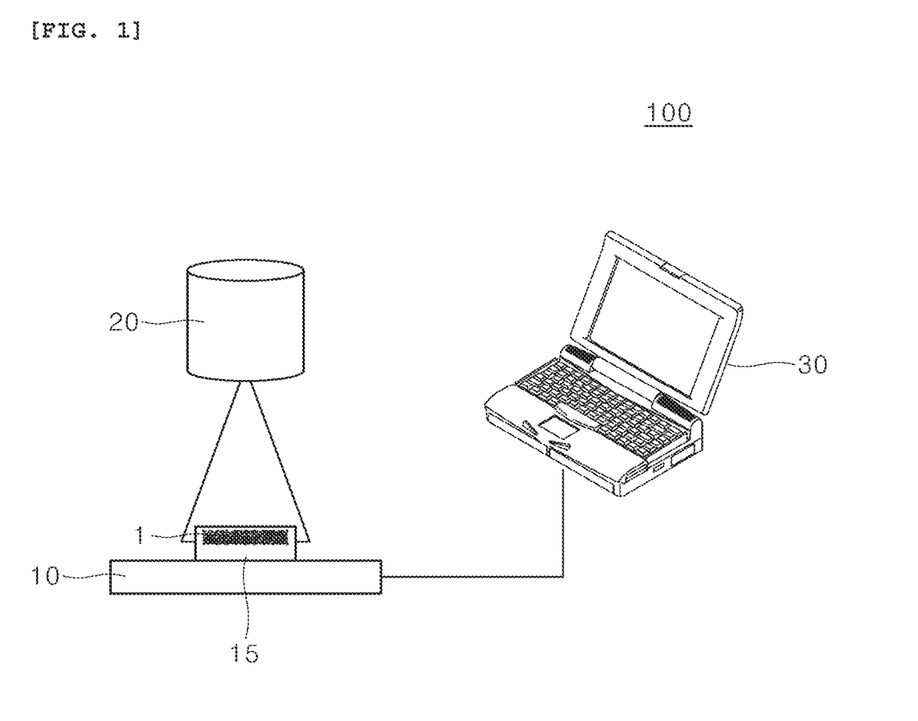
FIG. 1 is a diagram showing a concept of an ecotoxicity evaluation analysis device installed with a microalgae image analysis program therein according to the present invention.

FIG. 1 is a diagram showing the concept of an ecotoxicity evaluation analysis device 100 installed with a microalgae image analysis program therein in accordance with the present invention.

Figure 2:
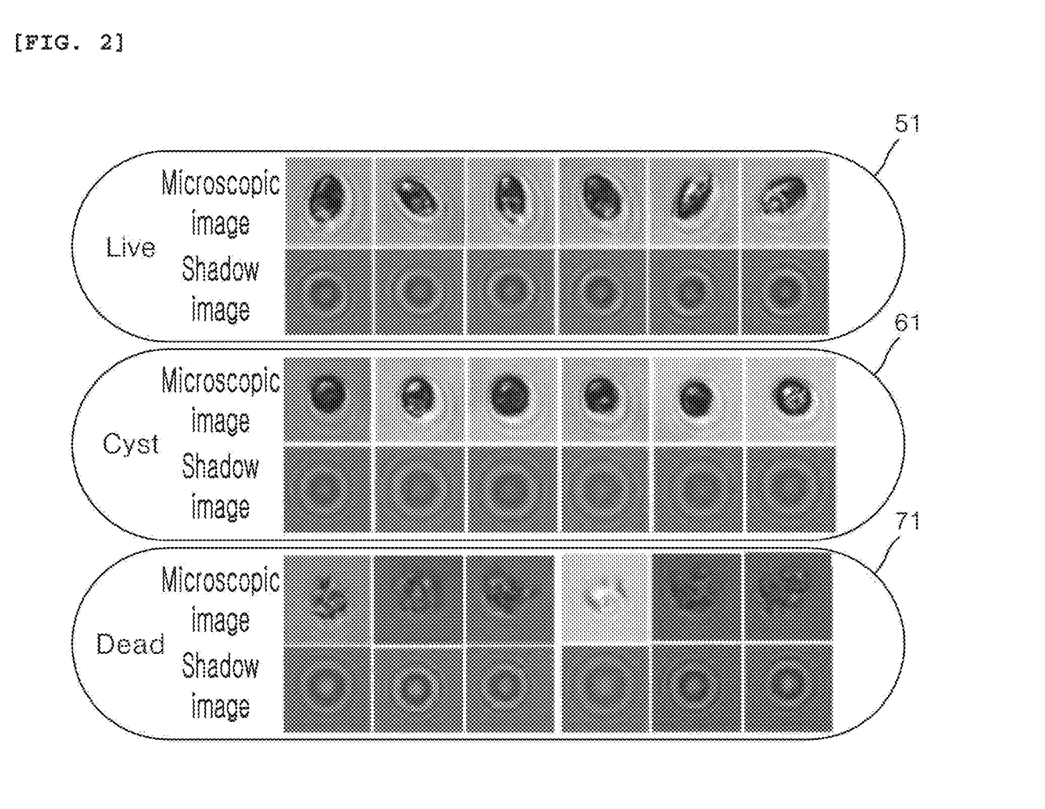
FIG. 2 is a photograph showing a microscopic image and a shadow image of the microalgae state of FIG. 1.

FIG. 2 is a photograph showing a microscopic image and a shadow image of the microalgae state of FIG. 1.

Figure 3:
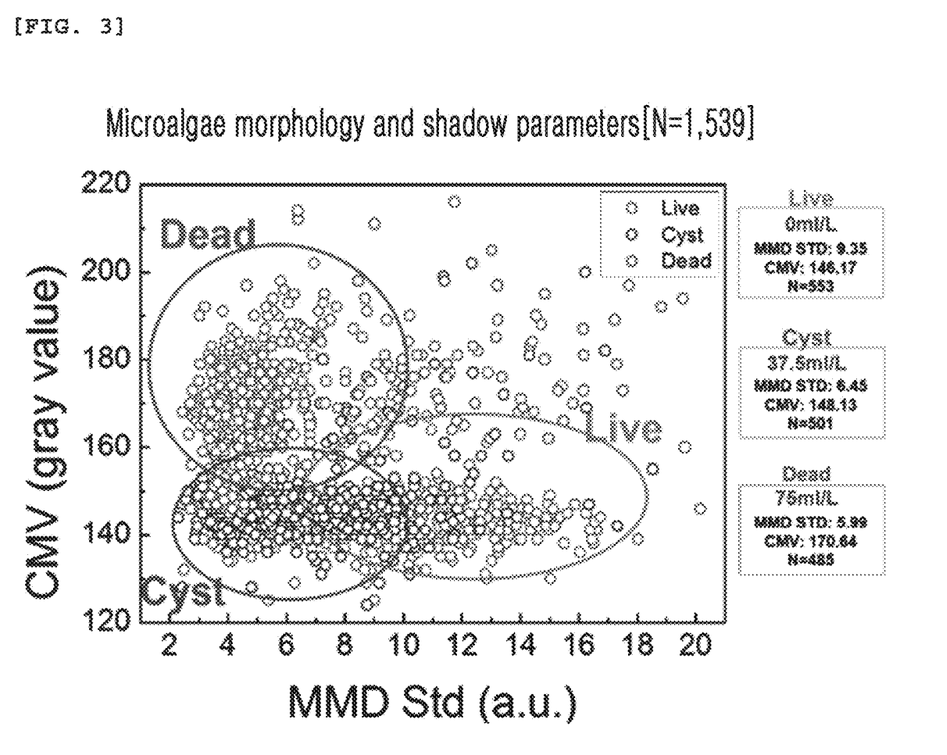
FIG. 3 is a graph showing microalgae morphology and shadow parameters of FIG. 1.

FIG. 3 is a graph showing microalgae morphology and shadow parameters of FIG. 1.

Figure 4:
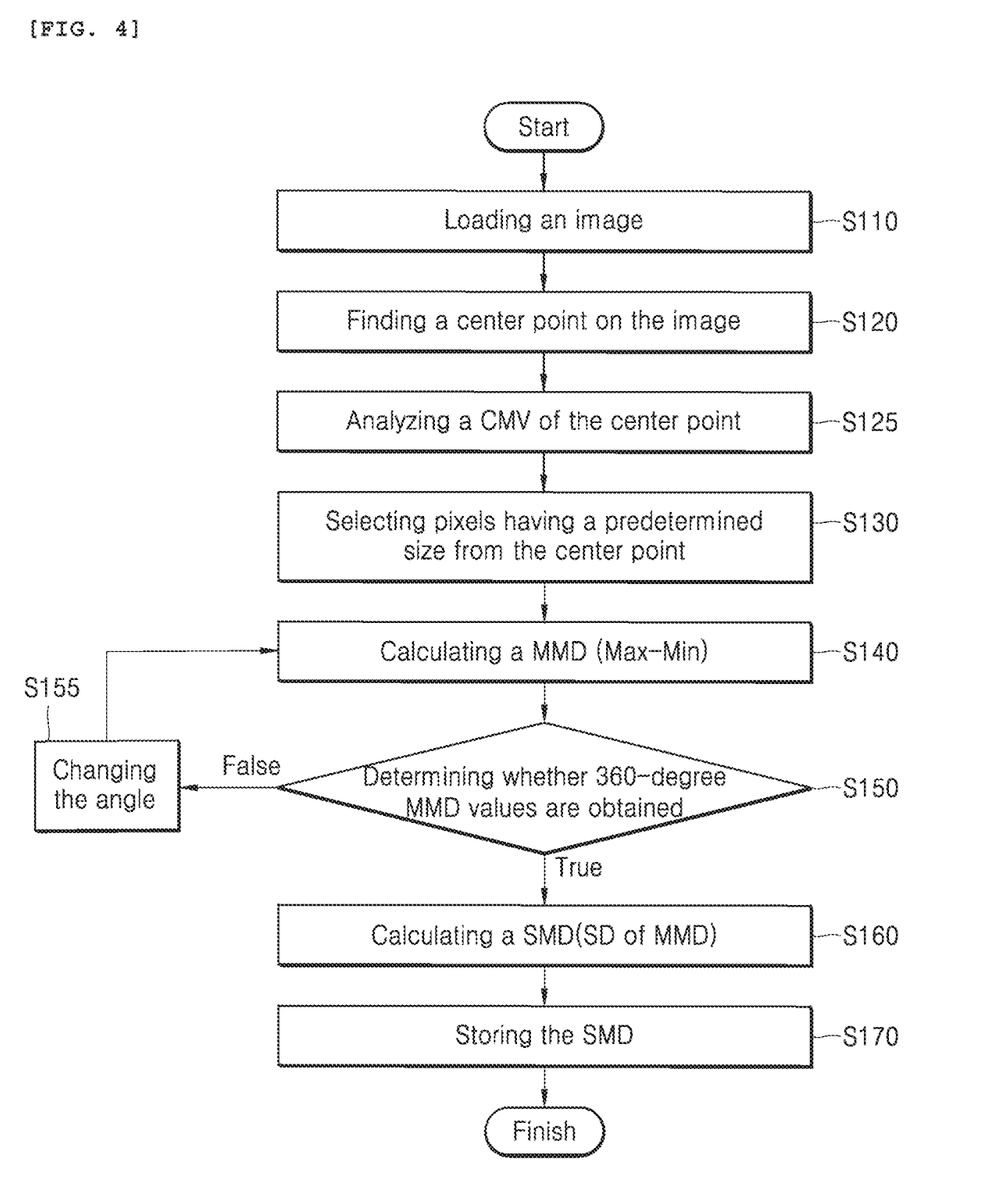
FIG. 4 is a flow chart of a process for evaluating and analyzing ecotoxicity of the present invention using an ecotoxicity evaluation analysis device installed with a microalgae image analysis program therein.

FIG. 4 is a flow chart of a process for evaluating and analyzing ecotoxicity using an ecotoxicity evaluation analysis device 100 installed with a microalgae image analysis program therein in accordance with the present invention.

Figure 5:
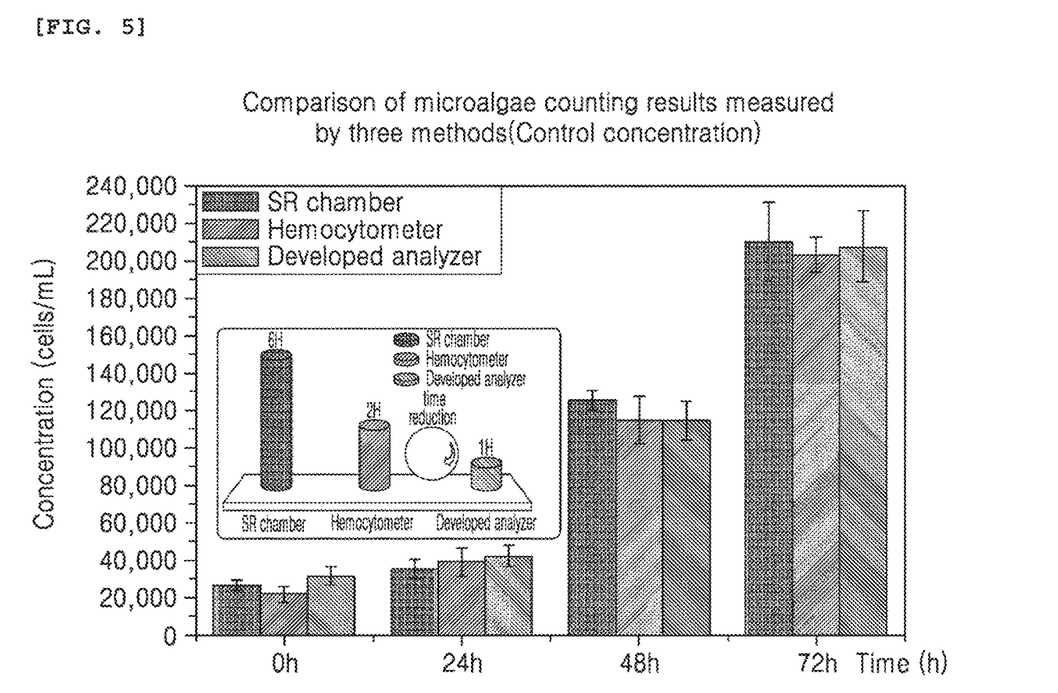
FIG. 5 is a graph comparing the verification results of the ecotoxicity evaluation analysis device of the present invention through the growth inhibition test (HNS; acetone) with the results of a standard manual analysis device.

FIG. 5 is a graph comparing verification results of the ecotoxicity evaluation analysis device of the present invention through the growth inhibition test (HNS; acetone) with the results of a standard manual analysis device.

Figure 6:
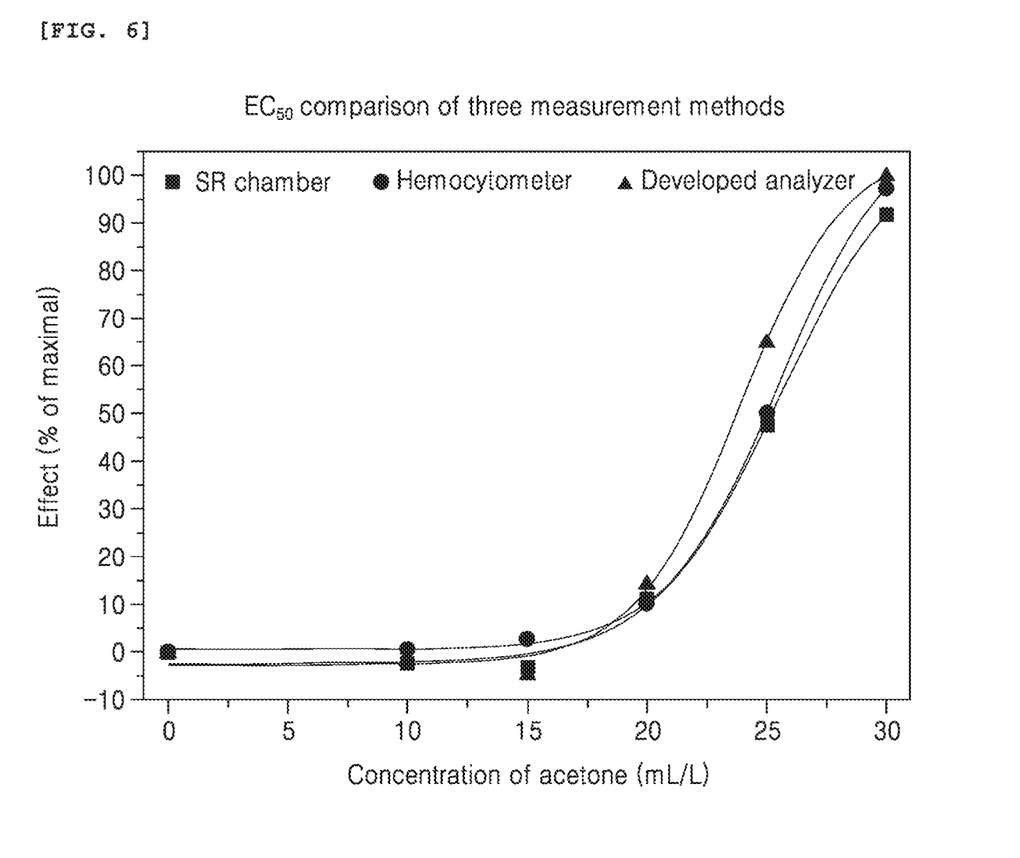
FIG. 6 is a graph showing the results of the ecotoxicity evaluation (EC50) comparing the verification results of the ecotoxicity evaluation analysis device of the present invention through the growth inhibition test (HNS; acetone) with a standard manual analysis method.

FIG. 6 is a graph showing the results of the ecotoxicity evaluation (EC50) comparing the verification results of the ecotoxicity evaluation analysis device of the present invention through the growth inhibition test (HNS; acetone) with a standard manual analysis method.

Figure 7:
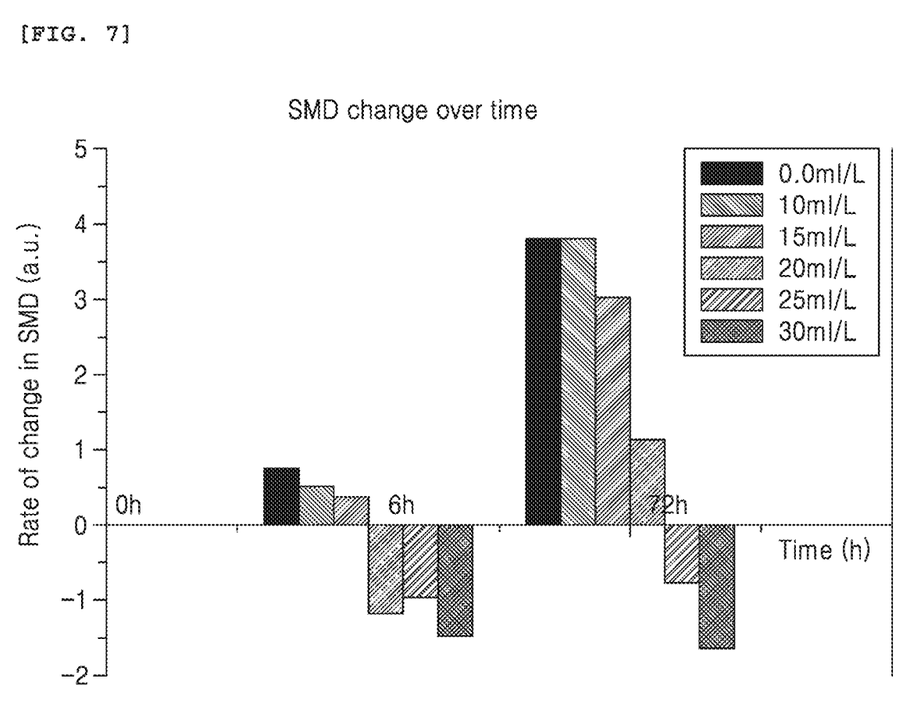
FIG. 7 is a graph showing the results of confirming the possibility of a technique for shortening the measurement of growth inhibition test later, which are the verification results of the ecotoxicity evaluation analysis device of the present invention through the growth inhibition test (HNS; acetone).

FIG. 7 is a graph showing the results of confirming the possibility of a technique for shortening the measurement of growth inhibition test later, which are verification results of the ecotoxicity evaluation analysis device of the present invention through the growth inhibition test (HNS; acetone).

The ecotoxicity evaluation analysis device 100 installed with the microalgae image analysis program therein according to the present invention will be described below.

The ecotoxicity evaluation analysis device 100 installed with the microalgae image analysis program therein according to one embodiment of the present invention is a device for analyzing the microalgae 1 and evaluating and analyzing an ecotoxicity, the device comprising; a complementary metal oxide semiconductor unit 10 having an arranging part 15 on the top for positioning the microalgae 1 and installed with a microalgae image analysis program therein for photographing a microscopic image and a shadow image of the microalgae 1 and analyzing the images; and a light emitting diode unit 20 for irradiating a light source to the microalgae 1 located in the arranging part 15 of the complementary metal oxide semiconductor unit 10.

Referring to FIG. 1, the ecotoxicity evaluation analysis device 100 installed with the microalgae image analysis program therein according to one embodiment of the present invention is realized by a simple structure wherein the arranging part 15 is provided on the top of the complementary metal oxide semiconductor unit 10, and the light emitting diode 20 irradiates the microalgae 1 after the microalgae 1 is positioned in the arranging part 15. In particular, the image obtained through the complementary metal oxide semiconductor unit 10 is analyzed with a dedicated analysis program to provide the user with the concentration and state results of the microalgae 1.

Referring to FIG. 2, the ecotoxicity evaluation and analysis device 100 installed with the microalgal image analysis program therein according to one embodiment of the present invention obtained the state of the microalgae 1 and the resulting image through the complementary metal oxide semiconductor unit 10.

The used microalgae 1 is *dunaliella tertiolecta*, and when exposed to stress (toxicity), transforms the state from the original form 51 into a cyst form 61 and loses mobility.

Furthermore, when the degree of stress is severe, the cell wall collapses and the state is transformed into a dead cell form 71.

By obtaining an image of the microalgae 1 under a microscope and a CMOS image changing accordingly, parameters for analyzing the shadow of the microalgae 1 were established as shown in FIG. 3.

Referring to FIGS. 3 and 4, they show the results of analyzing the concentration and state of the microalgae 1 by an algorithm according to one embodiment of the present invention shown in FIG. 4 using the ecotoxicity evaluation analysis device 100 installed with the microalgae image analysis program therein according to an embodiment of the present invention.

The analysis parameters used are Central Maxima Value (CMV) and Standard Deviation of MMD (SMD) values, each definition of which is included in FIG. 4. When 533 healthy microalgae 1, 501 cyst microalgae 1 and 485 dead microalgae 1 are analyzed by CMV and SMD values, they can be classified according to their respective states.

Although the states of the cell are not absolute and thus the boundary between the states may be ambiguous, the microalgae 1 in a healthy state is included in a green circle region, the microalgae 1 in a cyst state is included in a blue circle region, and the microalgae 1 in a dead state is included in a red circle region.

Upon analyzing this, when the microalgae 1 in a healthy state is exposed to stress, the SMD value becomes small, but there is no change in the CMV value. However, when cells die by exposure to more stress, the SMD value becomes smaller and the CMV value becomes larger. When the microalgae 1 in a dead state and the microalgae 1 in a cyst state are compared, the SMD value does not change, and the CMV value increases.

The analysis method using the ecotoxicity evaluation analysis device 100 installed with the microalgae image analysis program therein according to one embodiment of the present invention will be described below.

The analysis method using the ecotoxicity evaluation analysis device 100 installed with the microalgae image analysis program therein according to one embodiment of the present invention is a method for evaluating and analyzing an ecotoxicity using the ecotoxicity evaluation analysis device installed with the microalgae image analysis program therein, the method including the steps of: loading an image (step S110); finding a center point on the image (step S120); analyzing a CMV value of the center point (step S125); selecting pixels having a predetermined size from the center point to the right (step S130); calculating MMD (max-min) (step S140); determining the MMD value (step S150); calculating SMD (SD of MMD) when true in step S150 (step S160); storing the SMD (step S170); and changing the angle when the step of determining the MMD value in step S150 is false (step S155).

Referring to FIG. 4, the analysis method using the ecotoxicity evaluation analysis device 100 installed with the microalgae image analysis program therein according to one embodiment of the present invention is performed through the following steps:

loading the microscopic image and the shadow image of the microalgae 1 images photographed through the complementary metal oxide semiconductor unit 10 (step S110);

finding the center point through image analysis (step S120); analyzing the CMV value of the center point (step S125); and measuring a brightness of pixels having a predetermined size from the center point to the right (step S130).

Among them, the pixel having the maximum brightness and the minimum brightness is found and extracted. The discrepancy is named MMD (maxima minima distance) value (step S140).

Here, the MMD value is determined (step S150).

If it is determined in step S150 that the MMD value of 360 degrees is not secured and thus, the step S150 is false, the angle is changed by making an imaginary line on the pixels having a predetermined size from the center point to the right and using a function. A second MMD value is derived by selecting pixels having a predetermined size on the same line as the rotated line (step S155). As such, while rotating 360 degrees, multiple MMD values may be secured.

Steps S150 and S155 are repeated to obtain a 360-degree MMD value, and if step S150 is true, the standard deviation of the obtained MMD value is calculated (step S160). This is called a SMD (standard deviation of MMD) value.

The calculated SMD is stored (step S170).

Through the above steps, the analysis method using the ecotoxicity evaluation analysis device 100 installed with the microalgae image analysis program therein according to an embodiment of the present invention is finished.

Hereinafter, the operation of the ecotoxicity evaluation analysis device 100 installed with the microalgae image analysis program therein according to the present invention and the analysis method using the same will be described by way of examples.

Examples

The ecotoxicity evaluation analysis device 100 installed with the microalgae image analysis program therein according to the present invention and the analysis method using the same were applied to the evaluation of toxicity tests to confirm the performance thereof.

Acetone was used as a toxic substance. In a test method using an exponential formula, the temperature was maintained at 20° C., and the Irradiation was continuously performed using a white fluorescent lamp with an illuminance of 6,000 to 7,000 lx.

Three replicated plots were inoculated with an initial concentration of 20,000 cells/mL, and the shaking speed was set to 100 r/min. Non-toxic filtered seawater containing nutrient medium was used as a dilution water, and growth inhibition was analyzed for 72 hours.

The effective criteria for the evaluation of ecotoxicity are shown in Table 1.

TABLE 1

| Item | Condition |
| --- | --- |
| Test Method | Exponential Formula |
| Temperature | (20 ± 2) ° C. |

TABLE 1-continued

| Item | Condition |
| --- | --- |
| Light Source | White Fluorescent Light |
| Illuminance | (6,000~10,000)lx |
| Light cycle | Continuous lighting |
| Test container volume | 250 mL |
| Test substance capacity | 100 mL |
| Inoculation density | 10,000~20,000 cells/mL |
| Return | None |
| Number of replicated plot | 3-4 |
| Shaking speed | 100 r/min |
| Aeration | None |
| Dilution water | Non-toxic filtered seawater containing nutrient medium |
| Test period | 72 h |
| Test endpoint | Growth inhibition |

The experimental conditions in examples of the ecotoxicity evaluation analysis device 100 installed with the microalgae image analysis program therein according to the present invention and the analysis method using the same are shown in Table 2.

The experimental conditions satisfy the effective criteria for ecotoxicity evaluation.

TABLE 2

| Item | Condition |
| --- | --- |
| Test Method | Exponential Formula |
| Temperature | 20° C. |
| Light Source | White Fluorescent Light |
| Illuminance, | (6,000~7,000)lx |
| Light cycle | Continuous lighting |
| Test container volume | 250 mL |
| Test substance capacity | 100 mL |
| Inoculation density | 20,000 cells/mL |
| Return | None |
| Number of replicated plot | 3 |
| Shaking speed | 100 r/min |
| Aeration | None |
| Dilution water | Non-toxic filtered seawater containing nutrient medium |
| Test period | 72 h |
| Test endpoint | Growth inhibition |

Referring to FIG. 5, in an example of the microalgae analysis method using the ecotoxicity evaluation analysis device 100 installed with the microalgae image analysis program therein according to the present invention, the performance of the technology of the present invention was verified using representative SR chamber and hemocytometer of the microalgae analysis method as controls. Here, the concentration of the microalgae 1 contained in the sample was analyzed every 24 hours. Cells were dyed in the two controls, whereas measurements were performed without dyeing the cells in the present technology. In the controls, a microscope (200×) was used, and a microalgae 1 counting was performed manually by an experienced expert.

As a result, it can be confirmed that as compared to the analysis method of the controls, the automated technology of the present invention exhibits 2 times improved effect of reducing the measurement time compared to the hemocytometer and 6 times improved effect compared to the SR chamber.

When comparing the measurement errors between the hemocytometer and the technology of the present invention based on the SR chamber, the hemocytometer showed an error rate of 9.5% and the present technology showed an error rate of 12.075% as an average of four measurement errors. On the other hand, when the error rates of the SR chamber and the present technology are calculated based on the hemocytometer, the SR chamber showed an error rate of 10.58%, and the present technology showed an error rate of 13.68%.

In the example of the ecotoxicity evaluation and analysis device 100 installed with the microalgae image analysis program therein according to the present invention and the analysis method using the same, the error in counting (based on SR chamber) is shown in Table 3.

TABLE 3

|  | 0 h | 24 h | 48 h | 72 h |
|---|---|---|---|---|
| HemocytometerHemocytometer | 17% | 10% | 8% | 3% |
| Developed analyzerDeveloped Analyzer | 19% | 21% | 8% | 0.3% |

Referring to FIG. 6, a growth inhibition test using microalgae 1 is performed to obtain a 50% effective concentration (EC50) of a toxic substance. The 50% effective concentration is treated as an important data base for various toxicity analysis. When analyzing the results of the toxicity test performed with acetone, the SR chamber obtained a result of 25.6 mL/L, the hemocytometer obtained a result of 24.9 mL/L, and the present invention technology obtained a result of 24.2 mL/L.

In conclusion, the error rate of the present technology based on the SR chamber is 5.47%, and the error rate of the present technology based on the hemocytometer is 2.81%.

The experimental results in the example of the ecotoxicity evaluation analysis device 100 installed with the microalgae image analysis program therein according to the present invention re shown in Table 4.

TABLE 4

|  | SR chamber | Hemocytometer | Developed analyzer |
|---|---|---|---|
| EC$_{50}$ | 25.6 mL/L | 24.9 mL/L | 24.2 mL/L |
| Error Rate | Basis | 2.7% | 5.4% |

Referring to FIG. 7, the growth inhibition test is a test for determining the 50% effective concentration of a toxic substance, and thus, a high concentration (toxic concentration killing cells) of the toxic substance is not used therein. Therefore, there is no change in CMV as described in FIG. 3. However, the stress applied to the microalgae 1 increases with time of the exposure to the toxic substance, and thus the SMD value changes.

When comparing the SMD value at the time of 6 hours after exposure to the toxic substance and the SMD at the time of 72 hours after the completion of the growth inhibition test, it can be seen that the higher the toxic concentration, the lower the value.

This means that the oval-shaped *dunaliella tertiolecta* was deformed close to the circular shape. In other words, the oval cells having division and growth functions are transformed into dynamic, non-dividing circular cells. As a result, it can be quickly predicted that the greater the number of populations transformed into a circular cell, the lower the concentration of algae population to be measured later.

According to the present invention, a microalgae measurement device 100 using a complementary metal oxide semiconductor unit 10 and a light emitting diode 20 can be manufactured at low cost because an expensive light source, optical stage and optical lens are unnecessary.

According to the present invention, since an image taken with a complementary metal oxide semiconductor unit 10 is analyzed by image processing technology, it is possible to develop an automated analysis system. This drastically reduces the time spent for measurement by experts capable of evaluating ecotoxicity.

According to the present invention, by means of a complementary metal oxide semiconductor, the images are photographed in real time and the photographed images 51, 61 and 71 are analyzed, thereby eliminating the need for a process and reagent for fixing microalgae 1 (removing flagellar function).

According to the present invention, a technology capable of analyzing the state of microalgae 1 can analyze the microalgae by classifying it into a healthy state 51, a cyst state 61, and a dead state 71, respectively.

The technology of the present invention facilitates the classification of the microalgae between healthy state 51 and cyst state 61 occurring in the manual counting process which is currently performed by expert, and can classify the microalgae 1 in a dead state 71, which could be classified through a dyeing process, without a dyeing process.

According to the present invention, it is possible to automate cell state analysis and develop a dye-free device through the state analysis technology of microalgae 1.

According to the present invention, the state analysis technology of microalgae 1 dramatically shortens the time for analyzing the effects of toxic substances on the microalgae as well as the measurement time in a 96-hour acute analysis performed during the conventional ecotoxicity evaluation.

The conventional ecotoxicity evaluation measures dead or living populations and analyzes them to derive results. According to the present invention, however, the present technology can analyze changes in the state of microalgae 1 that occur when exposed to toxic substances, and, thus, can provide various research data that were not previously available. For example, the present invention can be applied to a study on the mechanism by which the microalgae 1 do not die and recover depending on the concentration of toxic substances, a study on the recovery ability of microalgae 1, etc.

Although various preferred embodiments of the present invention have been described above by way of some examples, it is to be understood that the description of various embodiments given in the "Detailed Description of the Embodiments" is merely exemplary; and that any person having ordinary knowledge in the technical field to which the present invention pertains can perform various modifications from the above descriptions without departing from the scope of the present invention or its equivalent scope.

In addition, it is to be noted that the present invention is not limited by the above descriptions because it can be implemented in various other embodiments; that the above descriptions are provided only to make the disclosure of the present invention complete, and only to enable those skilled in the art to fully understand the scope of the present invention; and that the scope of the present invention is defined only by each of the claims.

The invention claimed is:

1. An ecotoxicity evaluation analysis device installed with a microalgae image analysis program therein for analyzing microalgae 1 and evaluating and analyzing ecotoxicity, the device comprising: a complementary metal oxide semiconductor unit 10 having an arranging part 15 on the top for positioning the microalgae 1 and installed with the microalgae image analysis program therein for photographing a microscopic image and a shadow image of the microalgae 1 and analyzing the microscopic image and the shadow image; and a light emitting diode unit 20 for irradiating a light source to the microalgae 1 located in the arranging part 15 of the complementary metal oxide semiconductor unit 10, wherein the microalgae image analysis program is configured to:
calculate a CMV (Central Maxima Value) of a center point of a microalgae 1 image;
calculate a MMD (Maxima Minima Distance) by a difference between a maximum brightness and a minimum brightness among a predetermined number of a plurality of pixels from the center point;
calculate a SMD (Standard Deviation of MMD) on the basis of a standard deviation of the MMD; and
analyze the microalgae 1 by classifying it into a healthy state, a cyst state, and a dead state, respectively, on the basis of comparison of the CMV and the SMD, and wherein:
when the microalgae 1 is exposed to stress, the SMD of the healthy state becomes small but there is no change in the CMV value,
when the microalgae 1 dies by exposure to more stress, the SMD value becomes smaller and the CMV value becomes larger in the dead state, and
when the dead state and the cyst state are compared, the SMD value does not change, and the CMV value increases.

2. The ecotoxicity evaluation analysis device installed with a microalgae image analysis program therein according to claim 1, wherein the microalgae image analysis program analyzes the population of the microalgae 1 without using reagents.

3. The ecotoxicity evaluation analysis device installed with a microalgae image analysis program therein according to claim 2, wherein the microalgae image analysis program classifies and analyzes the state of the microalgae 1 without using reagents.

4. The ecotoxicity evaluation analysis device installed with a microalgae image analysis program therein according to claim 3, wherein the microalgae image analysis program uses automated image analysis technology.

5. A method for evaluating and analyzing ecotoxicity using an ecotoxicity evaluation analysis device installed with a microalgae image analysis program therein, the method comprising the steps of:
(a) loading an image;
(b) finding a center point on the image;
(c) analyzing a CMV(Central Maxima Value) of the center point;
(d) selecting a predetermined number of a plurality of pixels from the center point to the right;
(e) calculating a MMD (Maxima Minima Distance) by a difference between a maximum brightness and a minimum brightness among the plurality of pixels;
(f) determining whether 360/n MMDs are obtained by rotating n degrees;
(g) calculating a SMD(Standard Deviation of MMD) when 360/n MMDs are obtained by rotating 360/n times, n degrees per each time, a total of 360 degrees in step (f); and
(h) storing the SMD (step S170).

6. The method for evaluating and analyzing ecotoxicity using an ecotoxicity evaluation analysis device installed with a microalgae image analysis program therein according to claim 5, wherein, when the 360/n MMDs are not obtained by not rotating 360/n times, n degrees per each time, and a total of 360 degrees in step (f), the method further comprises the steps of: creating an imaginary line on a predetermined number of pixels from the center point to the right; rotating the imaginary line n degrees using a function; selecting a predetermined number of pixels on the same line as the imaginary line rotated n degrees to derive a second MMD; and repeating this step 360/n times to secure 360/n MMDs while rotating 360 degrees.

7. The method for evaluating and analyzing ecotoxicity using an ecotoxicity evaluation analysis device installed with a microalgae image analysis program therein according to claim 5, wherein the microalgae image analysis program analyzes the population of microalgae 1 without using reagents.

8. The method for evaluating and analyzing ecotoxicity using an ecotoxicity evaluation analysis device installed with a microalgae image analysis program therein according to claim 7, wherein the microalgae image analysis program classifies and analyzes the state of the microalgae 1 without using reagents.

9. The method for evaluating and analyzing ecotoxicity using an ecotoxicity evaluation analysis device installed with a microalgae image analysis program therein according to claim 8, wherein the microalgae image analysis program uses automated image analysis technology.

10. The method for evaluating and analyzing ecotoxicity using an ecotoxicity evaluation analysis device installed with a microalgae image analysis program therein according to claim 9, wherein the microalgae image analysis program analyzes the microalgae 1 by classifying it into a healthy state, a cyst state, and a dead state.

11. A non-transitory computer-readable recording medium storing a program for implementing the method for evaluating and analyzing ecotoxicity using an ecotoxicity evaluation analysis device according to claim 5.

* * * * *